United States Patent
Verhoff et al.

[19]
[11] Patent Number: 5,965,028
[45] Date of Patent: *Oct. 12, 1999

[54] PROCESS FOR TREATING A LIQUID

[75] Inventors: Francis H. Verhoff, Cincinnati, Ohio; Sanet Grond, Hennopspark; Fadl Hendricks, Kelvin, both of South Africa; Lakshminarayanan Pattabiraman Raman, Brooklyn Park, Mass.

[73] Assignee: Reilly Industries, Inc., Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/811,564

[22] Filed: Mar. 4, 1997

Related U.S. Application Data

[63] Continuation of application No. PCT/US96/12160, Sep. 12, 1995.

[30] Foreign Application Priority Data

Sep. 12, 1994 [ZA] South Africa ............................ 94/0711

[51] Int. Cl.$^6$ ............................ B01D 61/14; C07C 51/42
[52] U.S. Cl. ........................ 210/651; 210/656; 435/144; 562/580; 562/584
[58] Field of Search ................................... 562/580, 584; 435/144, 136; 210/651, 656, 659

[56] References Cited

U.S. PATENT DOCUMENTS

| | | | |
|---|---|---|---|
| 3,904,684 | 9/1975 | Tsuda | 260/535 P |
| 3,925,465 | 12/1975 | Nara | 562/580 |
| 4,048,225 | 9/1977 | Prescher | 562/580 |
| 4,113,771 | 9/1978 | Lawrence | 562/568 |
| 4,855,494 | 8/1989 | Margureanu | 562/580 |
| 5,032,686 | 7/1991 | Duflot | 562/580 |
| 5,045,459 | 9/1991 | Mothes et al. | 435/144 |
| 5,532,148 | 7/1996 | Datta et al. | 435/144 |
| 5,681,728 | 10/1997 | Miao | 435/136 |

FOREIGN PATENT DOCUMENTS

| | | | |
|---|---|---|---|
| 0 151 470 | 8/1985 | European Pat. Off. | 210/651 |
| A 0 479 084 | 4/1992 | European Pat. Off. | 210/651 |
| C 680 595 | 8/1939 | Germany | 210/651 |
| A 1 494 414 | 12/1977 | United Kingdom | 210/651 |

OTHER PUBLICATIONS

Raman, L.P. et al., "Consider Nanofiltration for Membrane Separations," (Mar. 1994) Chem. Engineering Progress, pp. 68–74.

Lesniak, W., "A Modified Method of Citric Acid Production," Chemistry, (1989) Polish Technical Review, pp. 17–19.

Primary Examiner—Ernest G. Therkorn
Attorney, Agent, or Firm—Woodard, Emhardt, Naughton Moriarty & McNett Patent and Trademark Attorneys

[57] ABSTRACT

A process for treating a liquid comprising subjecting a liquid containing, in solution, citric acid as well as a less desirable component having a similar molecular weight to citric acid, to nanofiltration in a filtration step. From the filtration step, a permeate in which the ratio of the concentration of the citric acid to that of the less desirable component is greater than the ratio of the concentration of the citric acid to that of the less desirable component in the solution, is obtained.

24 Claims, 1 Drawing Sheet

PROCESS FOR TREATING A LIQUID

CROSS-REFERENCE TO RELATED APPLICATIONS

This application is a continuation of PCT Application PCT/US96/12160, filed Sep. 12, 1995, designating the United States, which claims priority from South African application no. 94/0711, filed Sep. 12, 1994, both of which are incorporated herein by reference.

FIELD OF THE INVENTION

This invention relates to a process for treating a liquid. It also relates to a process for recovering citric acid.

SUMMARY OF THE INVENTION

According to a first aspect of the invention, there is provided a process for treating a liquid, which process comprises: (a) subjecting a liquid containing, in solution, citric acid as well as a less desirable component having a similar molecular weight to citric acid, to nanofiltration in a filtration step; and (b) obtaining, from the filtration step, a permeate in which the ratio of the concentration of the citric acid to that of the less desirable component is greater than the ratio of the concentration of the citric acid to that of the less desirable component in the solution.

In other words, there is a greater degree of rejection of the less desirable component than of the citric acid in the filtration step. The nanofiltration will normally involve contacting the liquid with a nanofiltration membrane. Nanofiltration will naturally also separate the citric acid from any component with a molecular weight which is significantly greater than that of citric acid.

The molecular weight or relative molecular mass of the less desirable component may be within 20% of that of citric acid. For example, the molecular weight of the less desirable component may be within 10%, and even within about 7%, of that of citric acid. In other words, the molecular weight of the second component may range from 0.8 MW–1.2 MW, e.g., 0.9 MW–1.1 MW, or even about 0.93 MW–about 1.07 MW, where MW is the molecular weight of the citric acid.

The Applicant believes that the process will have particular, but not necessarily exclusive, application in the treatment of fermentation broth to separate citric acid present therein as a fermentation product from residual glucose and/or fructose, thereby recovering the citric acid. It has been found that, with the process of the invention, the citric acid can be separated from residual glucose and/or fructose as well as other impurities such as medium and higher molecular weight by-products such as peptides and polysaccharides, produced by fermentation microorganisms, and which can be undesirable. In other words, the process has specific application in the recovery of citric acid from a fermentation broth, particularly from a clarified citric acid fermentation broth.

The clarified citric acid fermentation broth can typically be that obtained by fermenting a carbohydrate feedstock to produce citric acid-rich fermentation broth and waste solids, and separating the broth from the solids.

Citric acid has a similar molecular mass to glucose and fructose and can preferentially be separated from glucose and/or fructose in the process according to the invention, as a result of its greater permeability through the nanofiltration membrane as compared to that of glucose and/or fructose.

The filtration step may be carried out at a concentration of the citric acid in the broth of 5%–30% by mass, preferably 10%–20% by mass, and the nanofiltration may be carried out at a temperature of 10° C.–100° C., preferably 20° C.–50° C. The pressure drop across the nanofiltration membrane will depend on the nature of the membrane and one the nature of the citric acid and the less desirable component to be separated and can be established by routine experimentation.

The clarified citric acid fermentation broth may, before the filtration step, be subjected to cation exchange to remove cations, such as potassium and magnesium ions, therefrom.

The process may include further treating the citric acid solution from the filtration step to purify it and/or to obtain a more concentrated citric acid fraction, or solid citric acid or a derivative of citric acid, such as sodium citrate.

Thus, the citric acid solution from the filtration step may be purified by anion exchange, e.g., to remove traces of anionic impurities, and/or by contacting it with activated carbon to remove traces of organic matter.

The purified citric acid solution may then be concentrated. This may include treating the solution to obtain solid pure citric acid and residual mother liquor. The concentration may include subjecting the solution to at least one evaporation and crystallization sequence. In particular, the concentration may include passing the solution sequentially through an evaporator; a first crystallizer; a first centrifuge; optionally a dissolution tank, a second crystallizer and a second centrifuge; and producing mother liquor in the first centrifuge and, when present, in the second centrifuge. A portion of the mother liquor from the second centrifuge, when present, may then be recycled to the first crystallizer, while the mother liquor from the first centrifuge is withdrawn. The contacting of the citric acid solution with the activated carbon hereinbefore referred to may instead, or additionally, be effected after the purified citric acid solution has been concentrated at least partially, e.g., after it has passed through the evaporator.

The process may also include: (i) recycling a portion of the mother liquor from the first centrifuge to upstream of the evaporator; and/or (ii) withdrawing at least a portion of the mother liquor from the first centrifuge as a liquid product; and/or (iii) drying and/or granulating at least a portion of the mother liquor from the first centrifuge to obtain a solid citric acid/carbohydrate product; and/or (iv) treating at least a portion of the mother liquor from the first centrifuge, in a recovery step, to recover citric acid for recycle, or citrate salts as product.

When the process includes treating at least a portion of the mother liquid from the first centrifuge in a recovery step to recover citric acid, this citric acid may be recycled to upstream and/or downstream of the nanofiltration step. The treatment in the recovery step may then comprise one of the following: calcium citrate precipitation by adding lime thereto and redissolving with sulphuric acid; solvent extraction of citric acid utilizing a suitable solvent, followed by re-extraction of citric acid from the solvent into water using concentration differences or heating; ion exchange using a resin which selectively adsorbs citric acid, followed by elution; or various types of chromatography.

At least a portion of the retentate from the filtration step may be withdrawn as a liquid product. Instead, or additionally, at least a portion of the retentate from the filtration step may be dried or granulated to obtain a solid citric acid product. Instead, or additionally, at least a portion of the retentate from the filtration step may be treated in a citric acid recovery step, which may then be the same as the citric acid recovery step hereinbefore described, to recover citric acid or a derivative thereof therefrom.

The retentate from the filtration step may be combined with the mother liquor from the first centrifuge for withdrawal as a liquid product and/or for drying or granulating and/or for treatment in a recovery step, as hereinbefore described.

According to a second aspect of the invention, there is provided a process for recovering citric acid, which process comprises subjecting a clarified citric acid fermentation broth to nanofiltration in a filtration step to obtain, as a permeate, a purified citric acid solution.

The clarified citric acid fermentation broth may, before the filtration step, be subjected to cation exchange as hereinbefore described. The citric acid solution from the filtration step may be treated further to purify it and/or to obtain a more concentrated citric acid fraction, or solid citric acid or a derivative of citric acid, as hereinbefore described. The filtration step may also be as hereinbefore described.

The invention will now be described by way of example, with reference to the accompanying simplified flow diagram in FIG. 1 of a process according to the invention for treating a fermentation broth, and with reference to the non-limiting examples.

DETAILED DESCRIPTION OF THE INVENTION

Figure 1:
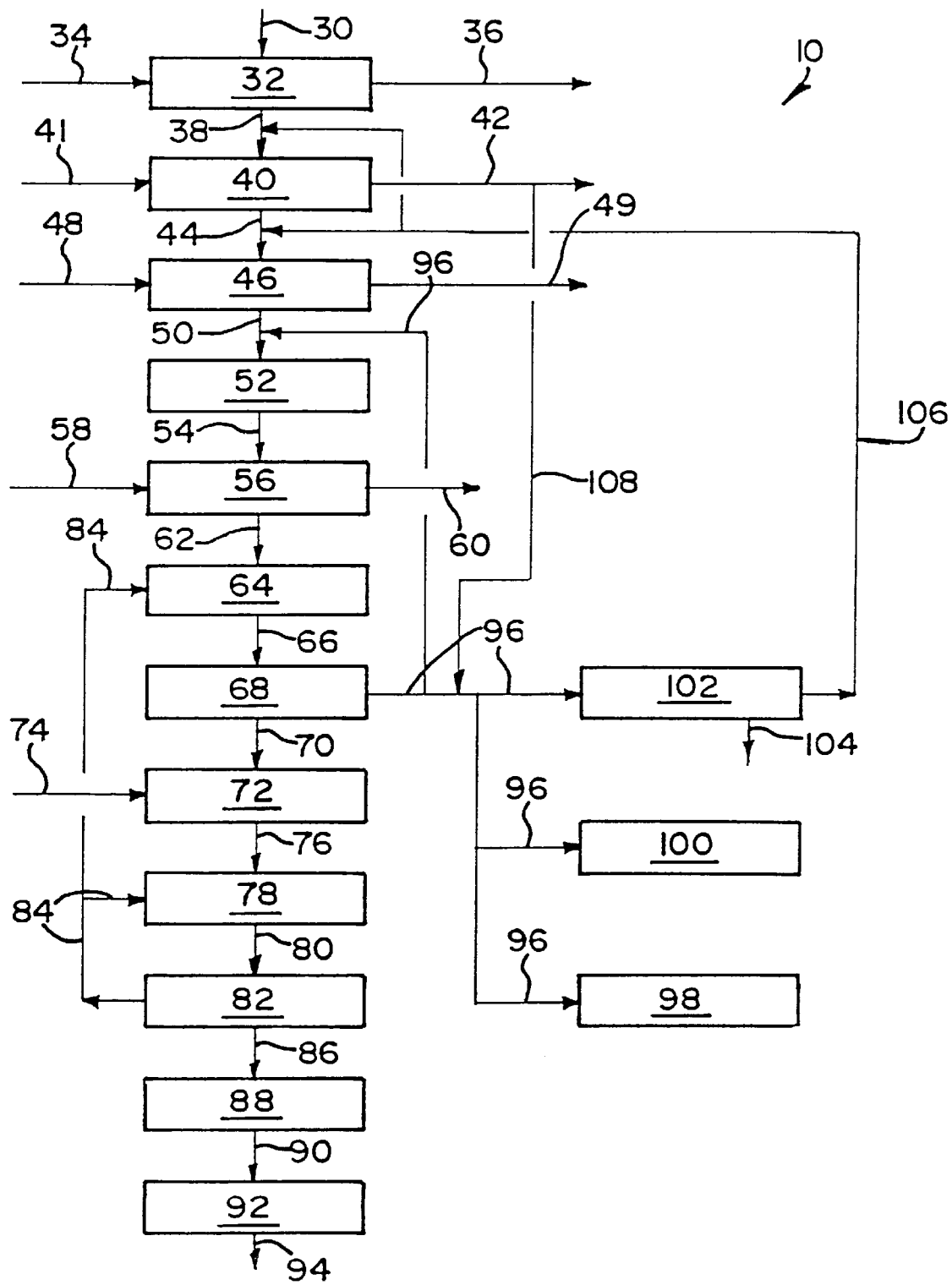
FIG. 1 is a flow diagram of a process for treating a fermentation broth.

In FIG. 1, reference numeral 10 generally indicates a process according to the invention for treating a fermentation broth.

The process 10 includes a cation exchanger stage 32. A clarified citric acid fermentation broth feed line 30 leads from a fermentation stage (not shown) into the stage 32. A regeneration water/acid flow line 34 also leads into the stage 32, while a waste product withdrawal line 36 leads from the stage 32. A flow line 38 also leads from the stage 32.

The flow line 38 leads to a nanofiltration step or stage 40, with a waste product or retentate withdrawal line 42 leading from the stage 40. A cleaning water/base and diafiltration flow line 41 leads into the nanofiltration stage 40. A filtrate flow line 44 leads from the stage 40 to an anion exchanger 46, with a regeneration water/base flow line 48 leading into the exchanger 46. A waste product withdrawal line 49 leads from the stage 46, while a flow line 50 leads from the exchanger 46 to an activated carbon bed stage 52.

A flow line 54 leads from the stage 52 to an evaporation stage 56, with a steam flow line 58 leading into the stage 56. A condensate line 60 leads from the stage 56. A flow line 62 leads from the stage 56 to a first crystallization stage 64. A flow line 66 leads from the crystallization stage 64 to a first centrifugation stage 68. A flow line 70 leads from the first centrifugation stage 68 to a dissolution tank 72, with a water make-up line 74 leading into the tank 72. A flow line 76 leads from the tank 72 to a second crystallization stage 78, with a flow line 80 leading from the second crystallization stage 78 to a second centrifugation stage 82. A mother liquor recycle line 84 leads from the stage 82 to the crystallization stages 64, 78. A flow line 86 leads from the second centrifugation stage 82 to a drier 88, with a flow line 90 leading from the drier 88 to a screening stage 92. A solid product withdrawal line 94 leads from the screening stage 92.

The second crystallization stage 78 and second centrifugation stage 82 are used to improve crystal quality and are optional; they can be dispensed with, if necessary.

A mother liquor withdrawal line 96 leads from the first centrifugation stage 68.

In a first embodiment of the invention, the line 96 can be routed back to the flow line 50 for recycling a portion of the mother liquor.

In a second embodiment of the invention, the flow line 96 can lead to a suitable liquid product withdrawal stage 98.

In a third embodiment of the invention, the flow line 96 can lead to a drying and granulation stage 100.

In a fourth embodiment of the invention, the flow line 96 can lead to a recovery stage 102. A waste product withdrawal line 104 leads from the stage 102. A citric acid recycle line 106 leads from the stage 102 back to upstream and/or downstream of stage 40.

It will be appreciated that the first, second, third and fourth embodiments described hereinbefore are optional and can be used individually, or a combination of two or more of the embodiments can be used, as desired.

A flow line 108 can, if desired, lead from the flow line 42 to the flow line 96 upstream of the product withdrawal stage 98, the drying and granulation stage 100, and/or the citric acid recovery unit 102.

In use, clarified citric acid fermentation broth, produced in known fashion in the fermentation stage, passes to the cation exchanger 32 where it is contacted with a suitable resin to remove cations such as calcium and sodium ions. If these ions are not removed they would form complexes with the citrate ions and be retained by the nanofilter element in the subsequent filtration stage 40 leading to product losses. The resin bed can be regenerated in known fashion, when required.

The broth then passes to the nanofiltration stage 40 where the citric acid is separated, by contacting the broth with a nanofiltration membrane, from glucose, fructose, and higher molecular weight components in the broth such as protein, residual anti-foaming agents, sucrose, peptides and polysaccharides which thus form the retentate. Smaller molecules as well as some anions pass through the nanofiltration membrane and, together with the citric acid and most of the water, form the permeate. The permeate is thus in the form of a purified citric acid solution in which the ratio or proportion of the concentration of citric acid to that of glucose and fructose is greater than the ratio or proportion of the concentration of citric acid to that of the glucose and fructose in the feed to the stage 40. Thus, in the filtration stage 40, glucose and fructose, which have a similar molecular weight (180) to citric acid (192) are separated therefrom. The permeate from the filtration stage 40 passes to the anionic exchanger 46 where anionic impurities are removed and withdrawn. The resin bed of the anionic exchanger 46 is regenerated in known fashion, when required.

The citric acid containing solution from the exchanger 46 passes to the activated carbon bed stage 52 where traces of organics are removed.

The citric acid solution thereafter passes to the evaporator where it is concentrated, using steam, from a concentration of 15% to 20% by mass citric acid, typically up to about 65% to 80% by mass citric acid. Condensate from the evaporation stage 56 leaves along the line 60. The concentrated citric acid solution passes to the first crystallization stage 64 where crystallization of the citric acid is effected. The stream then passes to the first centrifuge stage 68 where the citric acid crystals are separated from the mother liquor. The citric acid crystals pass into the dissolution tank 72 where they are redissolved in make-up water, whereafter they are recrystallized in the second crystallization stage 78 to improve crystal quality. The make-up water may be obtained from any suitable source, such as process condensate, a dilute citric acid stream, or the like. The stream from the crystallization stage 78 passes to the second centrifugation stage 82 where mother liquor is again removed. The moist crystals pass to the drier 88, with dried crystals passing to the screening stage 92. Dried solid substantially pure citric acid crystals are withdrawn along the flow line 94.

The crystallization stages 64, 78 typically comprise known crystallizers, and will thus include ancillary equipment normally associated therewith such as steam feed/condensate outlet lines, cooling fluid lines, and the like.

Mother liquor from the first centrifugation stage 68 is withdrawn along the flow line 96.

In a first embodiment, a portion of this mother liquor can be recycled to the activated carbon bed 52.

In a second embodiment, at least a portion of this mother liquor can be withdrawn as a liquid product in the stage 98.

In a third embodiment, at least a portion of this mother liquor can be dried and granulated in the stage 100 to obtain a citric acid/carbohydrate solid commercial product.

In a fourth embodiment, at least a portion of this mother liquor can pass to the recovery stage 102. Waste product, e.g., glucose and trace impurities, from the recovery stage 102 is withdrawn, while if pure citric acid is recovered, it may be recycled to upstream or downstream of stage 40; or if citrate salts are recovered, they will be recovered as product. A portion of the retentate from the nanofiltration stage 40 can be routed, by means of the flow line 108, to the stream 96 and then routed to any of the optional stages 98, 100 and/or 102, if desired, to recover residual citric acid or a derivative thereof present in this stream.

In one version of the invention, the recovery stage 102 may utilize calcium citrate precipitation after lime addition; followed by sulphuric acid addition to form citric acid as well as the by product gypsum, to recover citric acid.

In another version, the citric acid in the mother liquor may, in the stage 102, be extracted using a suitable solvent, followed by re-extraction of citric acid from the solvent phase into water using concentration differences or with the aid of heat.

In yet another version, the recovery stage 102 may comprise an ion exchange resin which selectively adsorbs citric acid, with elution of the product into water thereafter taking place.

In yet a further version of the invention, the citric acid recovery stage may comprise various types of chromatography.

The Applicant believes that with the process 10, citric acid can be recovered effectively and at relatively low cost. In addition, it is believed that the process 10 will be relatively simple to operate.

EXAMPLES

The following examples are provided for illustrative purposes, and are not intended to limit the scope of the invention as claimed herein. Any variations in the exemplified methods which occur to the skilled artisan are intended to fall within the scope of the present invention.

Example 1

The process 10 of the invention was simulated theoretically as follows:

Clarified citric acid fermentation broth containing 18.4 weight percent citric acid, can be obtained by fermentating various cultures, such as *Aspergillus niger*, on a purified carbohydrate feedstock, and filtering off the resultant biomass. The broth leaving the fermenters can contain 0.2% (w/w) unfermented glucose or 0.2% (w/w) unfermented fructose.

The clarified citric acid fermentation broth is then subjected to cation exchange, to remove cations such as potassium and magnesium ions.

The clarified decationized citric acid fermentation broth is then contacted with a nanofiltration membrane, and 80 or more percent of the citric acid transfers to the permeate, which contains up to 18 weight percent citric acid. The permeate also contains the following from the clarified decationized citric acid fermentation broth: a portion of the glucose and fructose, anions, cations, amino acids and sucrose, as well as 80 or more percent of the water. The retentate can be treated in a citric acid recovery step, using the UOP™ Citric Acid Sorbex™ Process (Citrex™), to recover the remaining citric acid.

The permeate from the nanofiltration step can be subjected to anion exchange, to remove traces of anionic impurities, followed by contacting with activated carbon, to remove traces of organics.

The permeate can thereafter be concentrated by evaporation in an evaporator, followed by a first crystallizer, a first centrifuge, a dissolution tank, a second crystallizer and a second centrifuge; with 20% by weight of the mother liquor from the second centrifuge being recycled to the first crystallizer, while the mother liquor from the first centrifuge is withdrawn.

The process can include (i) recycling 25% (w/w) of the mother liquor from the first centrifuge to upstream of the evaporator, (ii) withdrawing 10.0% (w/w) of the mother liquor from the first centrifuge as a liquid product, (iii) drying and granulating 21.6% (w/w) of the mother liquor from the first centrifuge to obtain a solid citric acid/carbohydrate product; and (iv) treating the remainder of the mother liquor from the first centrifuge, together with 80% (w/w) of the nanofiltration retentate, using the UOP™ Citric Acid Sorbex™ Process (Citrex™) process (this process revolves around any one of various chromatographic techniques, such as ion exclusion chromatography, whereby citric acid is separated from the feed stream by selective adsorption onto a solid adsorbent) in a recovery step, to recover citric acid which can be recycled to downstream of the nanofiltration step.

In the Citrex recovery step, which uses a very dilute solution of sulfuric acid as desorbent, the extract can contain, from the feed stream, on a weight to weight basis: 92% of the citric acid, 1% of the glucose and fructose, 1% of the cations and anions, 1% of the amino acids and biomass, negligible sulfuric acid, and 44% of the water from both the feed stream and the desorbent stream. The balance of the above mentioned components report to the raffinate (waste stream).

Example 2

In a simulation of the nanofiltration step or stage 40, laboratory scale tests were conducted on simulated citric acid fermentation broths containing, by mass, 18–19% citric acid, 1% lactose, 0.2% glucose and 0.05% yeast extract. The yeast extract was used to mimic other components normally present in commercial formation broths. Each test was conducted with a pair of membranes, by treating a batch of the simulated broth. Concentrations of each of the components were measured, and the rejections calculated. The results are set out in Tables 1, 2 and 3 (all percentages are on a mass bases).

TABLE 1

Results of Nanofiltration Test 1

| Experiment 1 | Citric Acid % | Lactose % | Glucose % |
|---|---|---|---|
| Feed | 18.8 | 0.88 | 0.22 |
| Permeate - Membrane A | 12.3 | 0.01 | 0.03 |
| Permeate - Membrane B | 14.6 | 0.18 | 0.09 |
| Concentrate | 29 | 2.1 | 0.47 |

Membrane A: Filmtec NF45 membrane obtained from Dow Liquid Separations in the USA or from Dow Deutschland Inc., Industriestrasse, 77836 Rheinmunster, Germany.
Membrane B: MPKW MPF21 membrane obtained from Membrane Products Kiryate Weizman Limited, Post Office Box 138, Rehovot 76101, Israel.

TABLE 2

Results of Nanofiltration Test 2

| Experiment 2 | Citric acid % | Lactose % | Glucose % |
|---|---|---|---|
| Feed | 18 | 0.88 | 0 |
| Permeate - Membrane A | 11.4 | 0.01 | none |
| Permeate - Membrane B | 11.7 | 0.05 | 0.07 |
| Concentrate | 28 | 1.9 | 0.38 |

TABLE 3

Rejections of the two membranes

| Rejections expressed as percentages | Citric acid % | Lactose % | Glucose % |
|---|---|---|---|
| Filmtec NF45 | | | |
| Test 1 | 34.6 | 98.9 | 86.4 |
| Test 2 | 36.7 | 98.9 | >90 |
| MPKW MPF23 | | | |
| Test 1 | 22.3 | 79.5 | 59.1 |
| Test 2 | 35.0 | 94.3 | 65.0 |

One of the key parameters in nanofiltration is the rejection. For the simulated citric acid fermentation broths, it was expected, according to literature and product information, that membrane rejections would be in the order lactose>citric acid>glucose. However, as can be seen from Table 3, the actual rejection of citric acid was surprisingly found to be lower than that of glucose.

This feature thus provides the basis for a simple and efficient means of separating citric acid from high and medium molecular weight impurities as well as removing most of the residual glucose, in respect of fermentation broth.

It is to be appreciated that, together with the citric acid, other more valuable fermentation products can be separated from the glucose.

We claim:

1. A process for treating a liquid, which process comprises subjecting a liquid containing, in solution, citric acid as well as a less desirable component having a molecular weight similar to that of citric acid, to nanofiltration in a filtration step;
   obtaining, from the filtration step, a permeate in which the ratio of the concentration of the citric acid to that of the less desirable component is greater than the ratio of the concentration of the citric acid to that of the less desirable component in the solution the permeate including 80 or more percent of the citric acid originally in said liquid; and
   concentrating the permeate by subjecting it to crystallization without treating the permeate to remove the remaining less desirable component prior to the crystallization.

2. A process according to claim 1, wherein the molecular weight of the less desirable component is within 20% of that of citric acid.

3. A process according to claim 2, wherein the molecular weight of the less desirable component is within 10% of that of citric acid.

4. A process of claim 1, wherein the molecular weight of the less desirable component is less than that of citric acid.

5. A process according to claim 4, wherein the liquid is clarified citric acid fermentation broth so that the permeate is a purified citric acid solution, and the less desirable component is glucose and/or fructose.

6. A process according to claim 5, wherein the filtration step is carried out at a concentration of the citric acid in the broth of 5%–30% by mass, and wherein the filtration is carried out at a temperature of 10° C.–100° C.

7. A process according to claim 5, wherein the clarified citric acid fermentation broth is, before the filtration step, subjected to cation exchange to remove cations therefrom.

8. A process according to claim 5, wherein the citric acid solution from the filtration step is purified by anion exchange and/or by contacting it with activated carbon.

9. A process according to claim 5, which includes concentrating the purified citric acid solution by subjecting it to crystallization.

10. A process according to claim 9, wherein the concentration is effected by passing the purified citric acid solution sequentially through an evaporator; a first crystallizer; a first centrifuge; optionally, a dissolution tank, a second crystallizer and a second centrifuge; and producing mother liquor in the first centrifuge and, when present, in the second centrifuge, with a portion of the mother liquor from the second centrifuge then being recycled to the first crystallizer, while the mother liquor from the first centrifuge is withdrawn.

11. A process according to claim 10, which includes (i) recycling a portion of the mother liquor from the first centrifuge to upstream of the evaporator; and/or (ii) withdrawing at least a portion of the mother liquid from the first centrifuge as a liquid product; and/or (iii) drying and granulating at least a portion of the mother liquor from the first centrifuge to obtain a solid citric acid/carbohydrate product; and/or (iv) treating at least a portion of the mother liquor from the first centrifuge, in a recovery step, to recover citric acid for recycle, or citrate salts as product.

12. A process according to claim 10, which includes treating at least a portion of the mother liquid from the first centrifuge, in a recovery step, to recover citric acid, with the citric acid being recycled to upstream and/or downstream of the nanofiltration step, and with treatment in the recovery step comprising one of the following: calcium citrate precipitation by adding lime thereto and redissolving with sulfuric acid; solvent extraction of citric acid utilizing a suitable solvent, followed by re-extraction of citric acid from the solvent into water using concentration differences or heating; ion exchange using a resin which selectively adsorbs citric acid, followed by elution; or chromatography.

13. A process according to claim 12, which includes (i) withdrawing at least a portion of the retentate from the filtration step as a liquid product, and/or (ii) drying or granulating at least a portion of the retentate from the filtration step to obtain a solid citric acid product, aid/or (iii) treating at least a portion of the retentate from the filtration step in a citric acid recovery step.

14. A process according to claim 1, wherein said less desirable component is glucose.

15. A process for treating a liquid, which process comprises providing a liquid containing, in solution, citric acid as well as a less desirable component having a similar molecular weight to citric acid, and cations;

removing cations from said liquid to form a cation-depleted liquid; subjecting said cation depleted liquid to nanofiltration in a filtration step;

obtaining, from the filtration step, a permeate in which the ratio of the concentration of the citric acid to that of the less desirable component is greater than the ratio of the concentration of the citric acid to that of the less desirable component in the solution;

concentrating the permeate by subjecting it to crystallization in at least one crystallizer, with citric acid crystals and mother liquor being produced in the crystallizer;

separating the citric acid crystals from the mother liquor;

treating at least a portion of the mother liquor to recover citric acid therefrom; and recycling at least a portion of the recovered citric acid to upstream and/or down stream of the filtration step.

16. A process according to claim 15, wherein the molecular weight of the less desirable component is within 20% of that of citric acid, and wherein the liquid is clarified citric acid fermentation broth so that the permeate is a purified citric acid solution, and the less desirable component is glucose and/or fructose.

17. A process according to claim 16, wherein the filtration is nanofiltration.

18. A process according to claim 16, wherein recovery of the citric acid is effected by means of chromatography.

19. A process according to claim 16, wherein the molecular weight of the less desirable component is less than that of citric acid.

20. A process according to claim 15, wherein said less desirable component is glucose.

21. A process for treating a liquid, which process comprises subjecting a liquid containing, in solution, citric acid as well as a less desirable component having a molecular weight less than that of citric acid, to nanofiltration in a filtration step; and obtaining, from the filtration step, a permeate in which the ratio of the concentration of the citric acid to that of the less desirable component is greater than the ratio of the concentration of the citric acid to that of the less desirable component in the solution the permeate including 80 or more percent of the citric acid originally in said liquid.

22. The process of claim 21 wherein the less desirable component is glucose and/or fructose.

23. A process according to claim 21, wherein said less desirable component is glucose.

24. A process according to claim 21, also including: subjecting said permeate to anion exchange.

* * * * *